Figure 1:
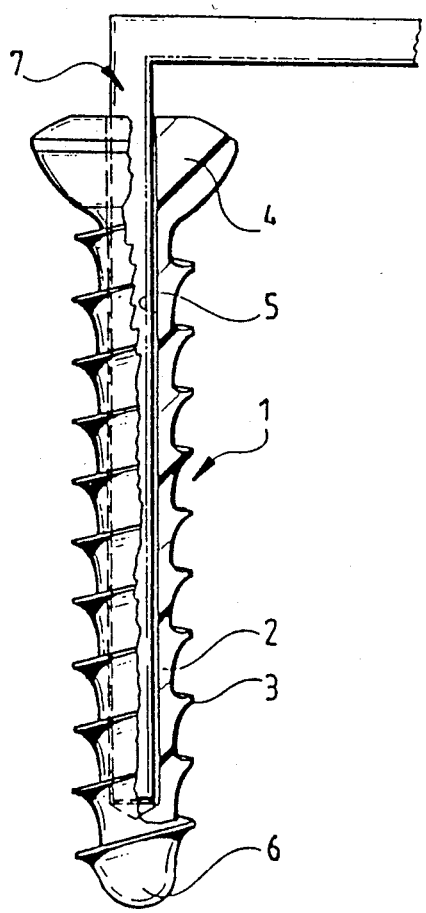

United States Patent
Mühling et al.

[11] Patent Number: 5,169,400
[45] Date of Patent: Dec. 8, 1992

[54] BONE SCREW

[75] Inventors: Joachim Mühling, Buchen; Theodor Lutze, Balgheim; Hans Pistner, Würzburg; Achim Hurst, Tuttlingen, all of Fed. Rep. of Germany

[73] Assignee: Aesculap AG, Fed. Rep. of Germany

[21] Appl. No.: 585,123

[22] PCT Filed: Mar. 30, 1989

[86] PCT No.: PCT/EP89/00344
§ 371 Date: Nov. 9, 1990
§ 102(e) Date: Nov. 9, 1990

[87] PCT Pub. No.: WO89/09030
PCT Pub. Date: Oct. 5, 1989

[30] Foreign Application Priority Data
Apr. 2, 1988 [DE] Fed. Rep. of Germany ....... 3811345

[51] Int. Cl.⁵ .............................................. A61B 17/58
[52] U.S. Cl. ........................................ 606/73; 606/72; 606/77
[58] Field of Search ............ 606/72, 73, 53, 60, 606/62, 64, 65, 67, 74, 75, 76, 77

[56] References Cited

U.S. PATENT DOCUMENTS

| 324,768 | 8/1985 | Hunt | 606/72 X |
| 2,112,007 | 3/1938 | Adams | 606/72 X |
| 3,103,926 | 9/1963 | Cochran et al. | 606/73 |
| 3,990,438 | 11/1976 | Pritchard | 606/73 |
| 4,013,071 | 3/1977 | Rosenberg . | |
| 4,101,984 | 7/1978 | MacGregor | 606/72 |
| 4,468,200 | 8/1984 | Münch | 606/73 X |
| 4,539,981 | 9/1985 | Tunc | 606/72 X |

FOREIGN PATENT DOCUMENTS

| 0213479 | 3/1987 | European Pat. Off. . | |
| 0260222 | 7/1987 | European Pat. Off. . | |
| 2036512 | 3/1972 | Fed. Rep. of Germany . | |
| 2945886 | 5/1981 | Fed. Rep. of Germany . | |
| 3434807 | 12/1985 | Fed. Rep. of Germany . | |
| 3513997 | 10/1986 | Fed. Rep. of Germany . | |
| 739089 | 1/1933 | France | 606/73 |
| 1477637 | 3/1967 | France . | |
| 637683 | 5/1950 | United Kingdom . | |
| 2084468 | 4/1982 | United Kingdom . | |

Primary Examiner—Robert A. Hafer
Assistant Examiner—Sam Rimell
Attorney, Agent, or Firm—Barry R. Lipsitz

[57] ABSTRACT

In order to reduce the risk that a bone screw, in particular one made of resorbing plastic material, with an externally threaded shaft will be destroyed by high screw-in torques, it is proposed that an insertion channel open at the top, arranged concentrically with the shaft and extending along most of the length of the shaft be located in the shaft for an insertion tool and have a cross-section which is non-circular and corresponds to the cross-section of the screwing-in tool.

15 Claims, 4 Drawing Sheets

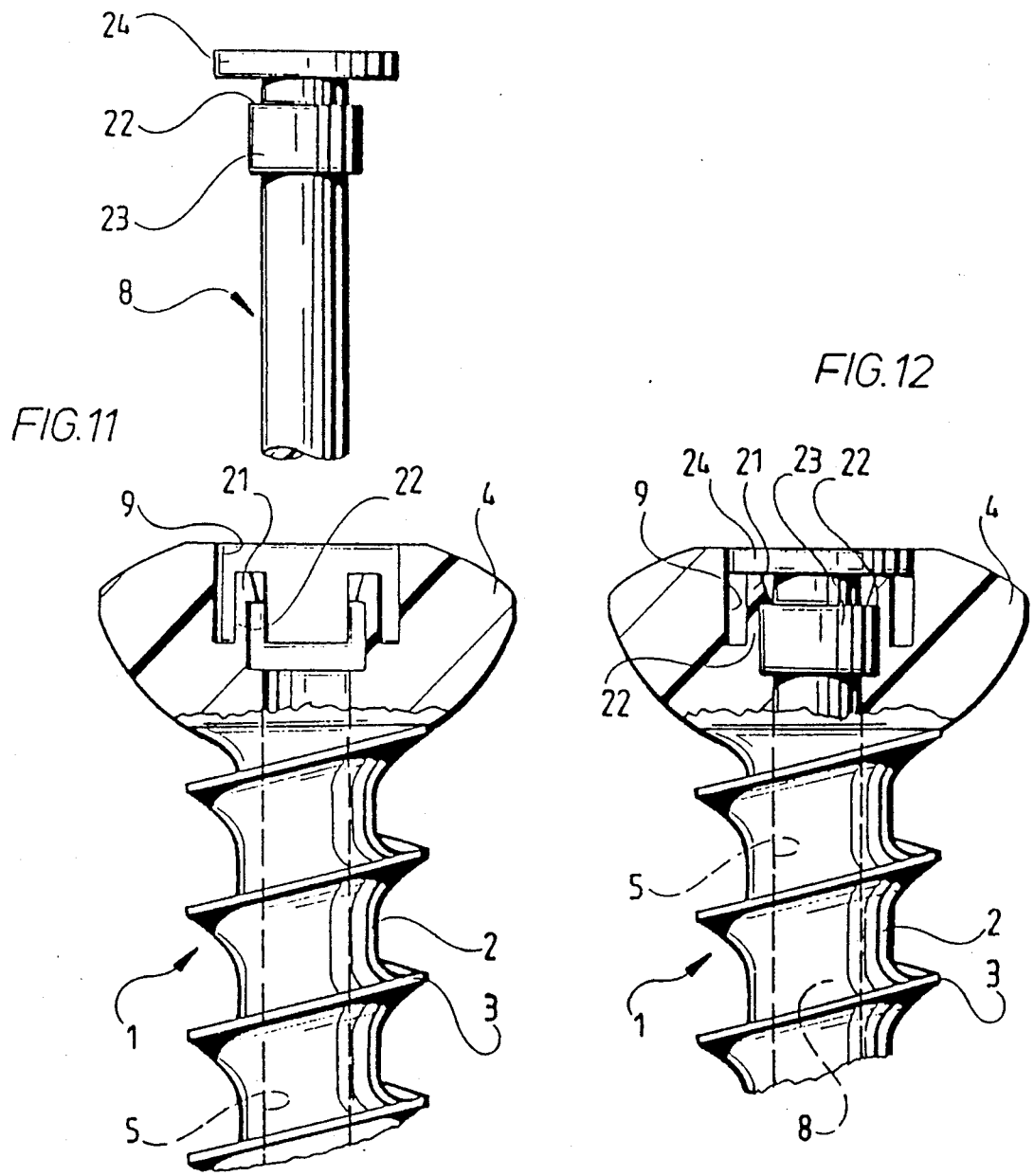

BONE SCREW

The invention relates to a bone screw made of resorbing plastic material and comprising an externally threaded shaft in which an insertion channel open at the top, arranged concentrically with the shaft and extending along most of the length of the shaft is located for a screwing-in tool, the cross-section of the insertion channel being non-circular and corresponding to the cross-section of the screwing-in tool.

Hitherto, bone screws for joining implants to bone substance or for joining adjacent bone fragments have mainly been made of stainless steel or titanium. Owing to the mechanical properties of this material, these constructions exhibit a high strength which enables the construction to be based on screws for wood and sheet metal processing. However, a disadvantage of such screws is that after completion of the healing process, they have to be removed from the body again, i.e., a further operation is necessary.

Recently, bone screws made of plastic material, in particular of resorbing plastic material, for example, of polylactide or poly-L-lactide have become known. These have the great advantage that after completion of the healing process, they are resorbed by the body, thereby making an additional operation for removal of such implants superfluous. With such plastic screws it has, however, proven disadvantageous that the plastic material exhibits substantially lower strength than conventional steel or titanium screws. There is, therefore, the danger that on screwing such bone screws into pre-drilled and pre-cut threaded holes, the plastic screw will be twisted off by the torsional tension exerted by the screwdriver on the plastic screw and thereby destroyed. This can be counteracted to a certain extent by using altered core diameters, flank angles and thread pitches, however, in spite of these measures, it is not always possible to avoid destruction of the screws when these are screwed in with hexagon socket, slotted or Phillips screwdrivers which engage the head of the bone screw in the conventional manner.

The danger of such a bone screw made of resorbing material shearing off is prevented in a known bone screw by the latter comprising an insertion channel extending over the entire length of the screw shaft for a non-circular screwing-in tool which thus comes to rest in a positively connected manner against the wall of the insertion channel along the entire length of the shaft. The torque introduced into the screw is thereby distributed over the entire length of the shaft (DP-A-0260222). However, a disadvantage is that this results in a weakening of the firmness of the bone screw after insertion in the bone. The resorption of the plastic material starts at the surface and with such a bone screw, therefore, quickly leads to disintegration of the plastic material of large molecular weight.

The object underlying the invention is to so design such a bone screw in spite of a continuous insertion channel in the shaft that the firmness of the bone screw is maintained as long as possible, even when resorption of the screw material starts to take place.

This object is accomplished in accordance with the invention with a bone screw of the kind described at the beginning in that a closure pin made of resorbing material is inserted in the insertion channel, thereby filling it out completely, the dimensions of the cross-section of the closure pin being such that it does not expand the screw.

The closure pin not only prevents undesired entry of body fluid and other body substances into the insertion channel but also increases the strength of the bone screw and so a weakening of the bone screw which might possibly result from the formation of an insertion channel is substantially eliminated again.

The insertion channel may be closed at the screw-in end of the bone screw. The screw-in depth of the screwing-in tool is thereby fixed, i.e., in this case the position of the screwing-in tool in the insertion channel is precisely defined.

In another embodiment, the insertion channel may penetrate the bone screw completely. This has the advantage that the shaft is correspondingly reinforced along its entire length and the screwing-in force is uniformly distributed throughout the entire length of the shaft.

In a preferred embodiment, provision is made for the cross-section of the insertion channel to be an equilateral triangle. In this embodiment, the cross-section of the shaft is weakened to a particularly slight extent. It is, however, also possible to use cross-sections in the shape of a rectangle, in particular a square, a regular polygon or a star.

Furthermore, provision may be made for the shaft to have a head-shaped widening at one end and for the insertion channel to extend through the widening. Such a head-shaped widening serves as stop for the screw-in depth of the bone screw.

In a first embodiment, the closure pin is fixable in the insertion channel with a press fit, with the insertion channel or the closure pin preferably tapering or widening in cross-section in the direction of insertion. When the closure pin is inserted, it will, therefore, clamp itself against the inside wall of the insertion channel and thereby be fixed permanently in the insertion channel.

In another embodiment, provision is made for the closure pin to be adhered or welded to the bone screw in the insertion channel.

In another embodiment, the closure pin is fixable in a positively connected manner by an elastic detent connection in the insertion channel. In all cases, the closure pin can carry a widening which delimits its screw-in depth, and a detent connection is preferably arranged in the region of the widening of the closure pin.

It is also expedient for the closure pin or the bone screw to be slotted in the axial direction in the region of the detent connection. This facilitates the insertion motion of the closure pin as the parts of the bone screw and the closure pin which rest against one another are elastically bendable in relation to one another owing to the slots.

Figure 2:
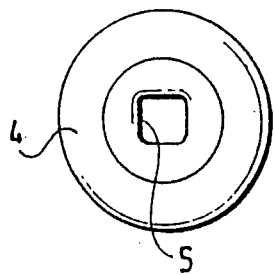
Figure 4:
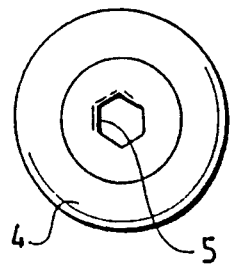
Figure 3:
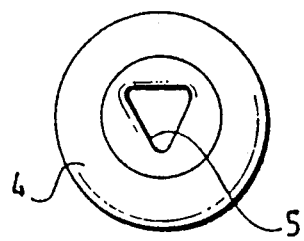
Figure 5:
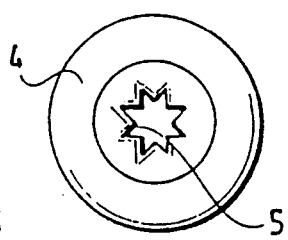
Figure 5:
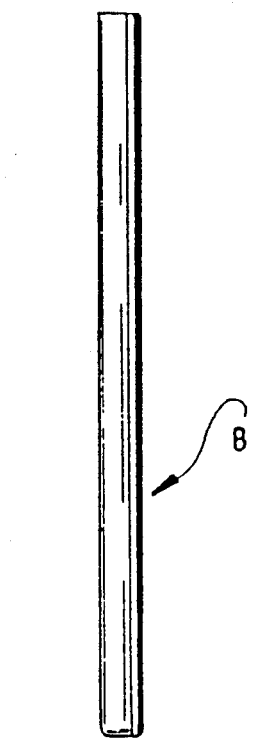
Figure 6:
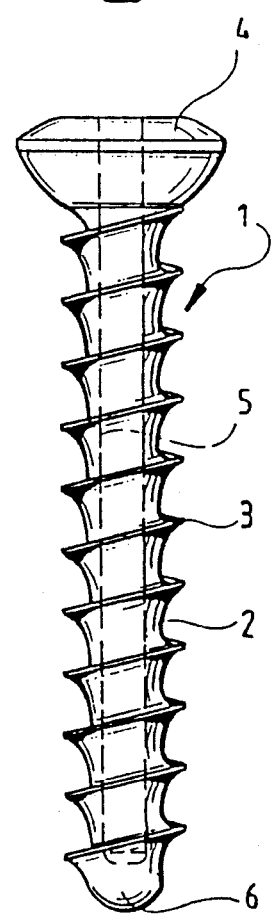
Figure 7:
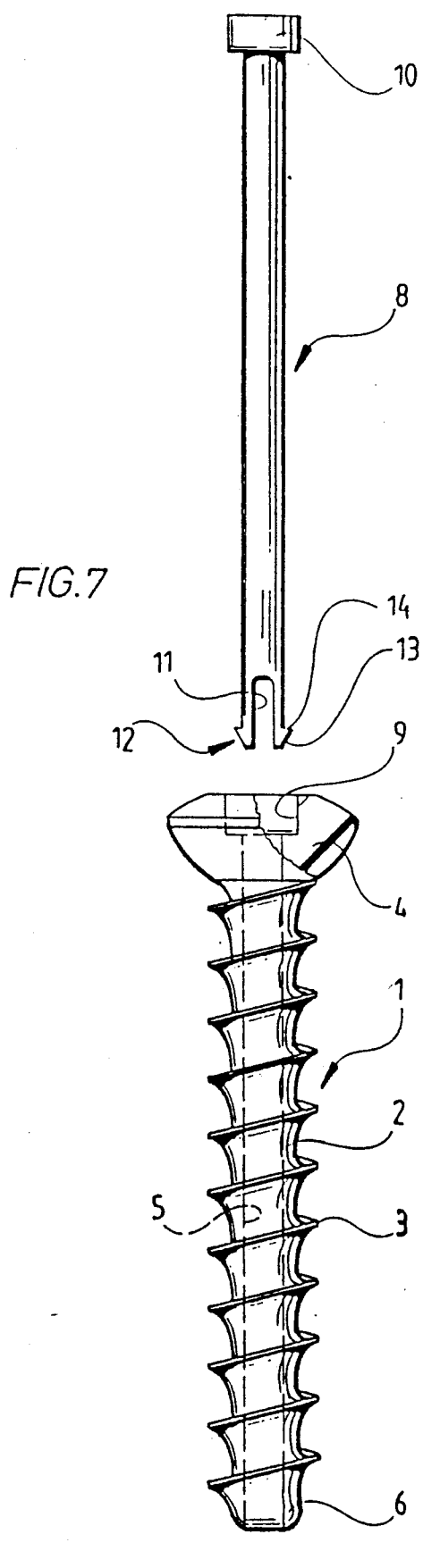
Figure 8:
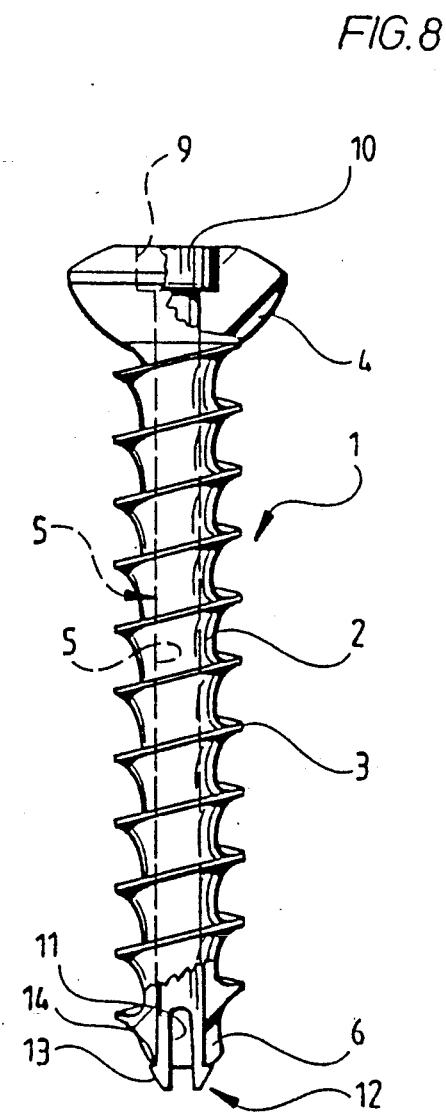
Figures 9, 10:
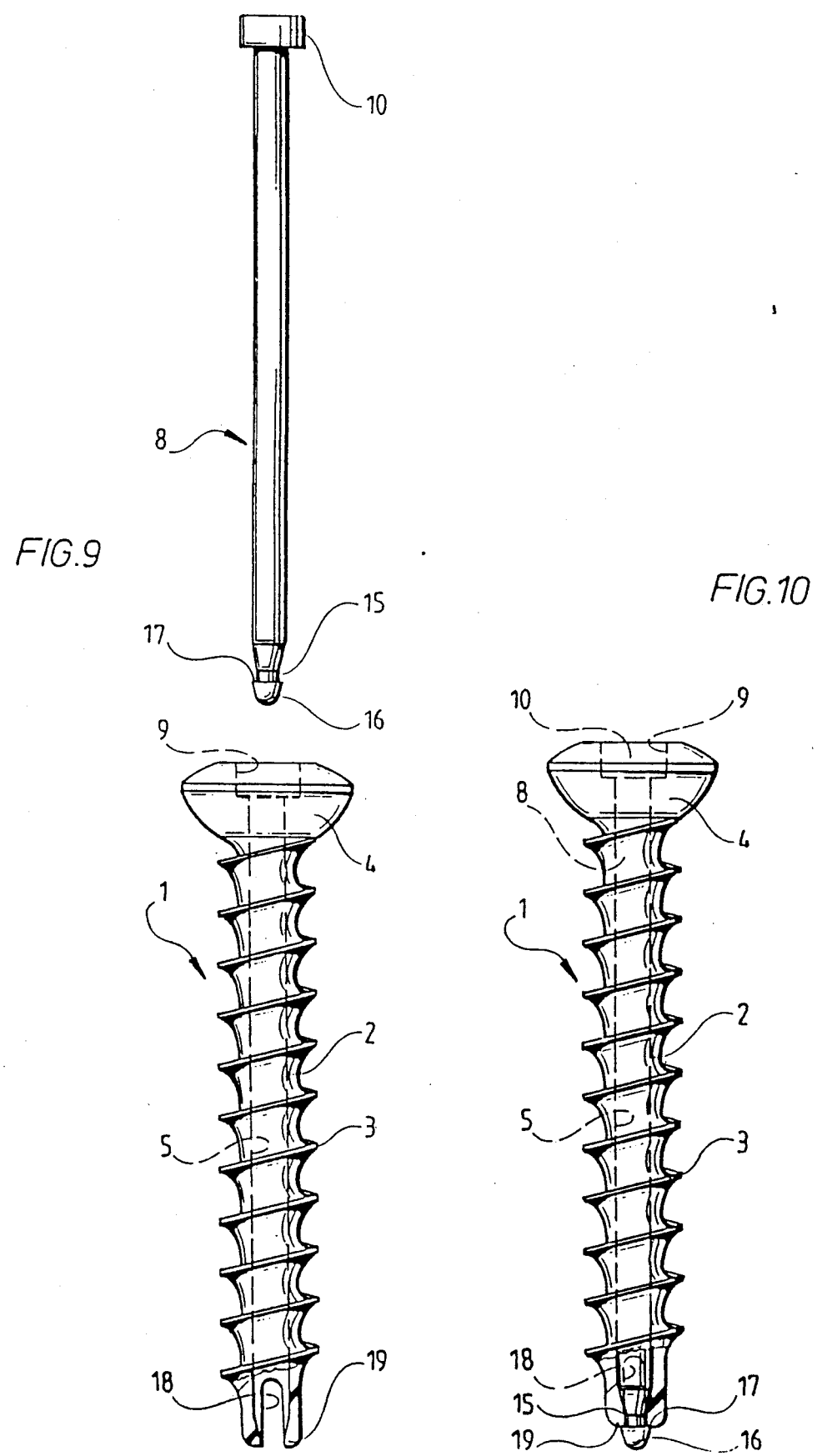

The following description of preferred embodiments serves in conjunction with the drawings to explain the invention in further detail. The drawings show:

FIG. 1 a bone screw in a partly broken-open illustration with a screwing-in tool inserted therein;

FIG. 2 a plan view of a first preferred embodiment of a bone screw with an insertion channel of square cross-section;

FIG. 3 a view similar to FIG. 2 with an insertion channel of triangular cross-section;

FIG. 4 a view similar to FIG. 2 with an insertion channel of hexagonal cross-section;

FIG. 5 a view similar to FIG. 2 with an insertion channel of star-shaped cross-section;

FIG. 6 a bone screw with a matching closure pin;

FIG. 7 a view similar to FIG. 6 with a closure pin slotted at the bottom end and with detent noses;

FIG. 8 a view of the bone screw of FIG. 7 with the closure pin in the inserted and engaged position;

FIG. 9 a view similar to FIG. 7 with a modified, engageable closure pin;

FIG. 10 a view of the bone screw of FIG. 9 with the closure pin in the engaged position;

FIG. 11 a view of the top part of a bone screw cut in the head region and of the top part of a closure pin; and FIG. 12 a view of the top part of the bone screw of FIG. 11 with the closure pin inserted therein.

The bone screw 1 illustrated in FIG. 1 comprises a shaft 2 with threads 3 and a widened head 4. A central insertion channel 5 extends through the head 4 into the interior of the shaft 2 as far as almost the screw-in end 6 of the bone screw. The insertion channel 5 exhibits throughout its entire length a constant, non-circular cross-section. The cross-section preferably has the shape of an equilateral triangle, as illustrated in FIG. 3. In other embodiments, the cross-section may have the shape of a rectangle, in particular a square (FIG. 2), the shape of a regular polygon, for example, a hexagon (FIG. 4) or the shape of a star (FIG. 5).

Into the insertion channel 5 which is open at the head there can be inserted a screwing-in tool 7 which is usually complementary in design to the cross-section of the insertion channel 5 and thereby establishes a positive connection with the side walls of the insertion channel 5. The screwing-in tool 7 is inserted throughout the entire length of the insertion channel 5 and hence extends along most of the length of the shaft 2. When the screwing-in tool 7 is turned about the longitudinal axis of the bone screw 1, a rotary connection is established by frictional contact between screwing-in tool and bone screw, with the force being introduced uniformly throughout the entire length of the insertion channel, i.e., the screwing-in force is distributed over the entire length. Since a material with high strength, for example, steel can be used as screwing-in tool 7, it is thereby possible, even with relatively low shear strength of the bone screw material, to exert large torsional forces on the screw without risking destruction of the bone screw. Above all, the turning forces can also be optimally introduced into that region in which the largest torsional forces occur at that moment because threads are being screwed into bone material in that region. The part of the screwing-in tool acting as stable core additionally reinforces the overall firmness of the bone screw during the screwing-in operation.

After the screwing-in, the screwing-in tool 7 can be easily pulled out of the insertion channel again.

In the embodiment illustrated in FIG. 1, the insertion channel 5 is closed at the screw-in end 6. It is, however, also possible for the insertion channel 5 to be of continuous design.

A closure pin 8 is provided for closing the blind-hole-like insertion channel 5. After the bone screw has been screwed in by the screwing-in tool 7, the closure pin 8 can be inserted into the insertion channel 5 and closes the latter outwardly. In the simplest case illustrated in FIG. 6, the closure pin 8 is of cylindrical design and corresponds in length to the length of the insertion channel 5. The cross-section of the closure pin 8 preferably corresponds to the cross-section of the insertion channel 5 and so the closure pin 8 fills out the insertion channel 5 completely. Like the bone screw which preferably consists of resorbing material, the closure pin 8 may be made of resorbing material and, in particular, it is expedient for bone screw and closure pin to consist of the same material. This material may also be reinforced by fibers embedded therein.

In order to fix the closure pin 8 in the insertion channel 5, the latter may be of such dimensions that it is held with a clamping or frictional fit in the insertion channel. For this purpose, it is also possible to reduce the cross-section of the insertion channel in the direction of insertion or to enlarge the closure pin 8 in cross-section at its rear end so that clamping only occurs when the closure pin has been inserted almost fully in the insertion channel 5.

Instead of being fixed by a clamping or frictional fit, the closure pin can be adhesively attached to the bone screw, for example, with a fibrin adhesive that causes no irritation of the tissue.

Another possibility of permanently fixing the closure pin in the insertion channel 5 is by welding. If the bone screw and the closure pin are heated in the head region of the bone screw, the two parts can be welded together in this region.

A special type of welding is usable when the closure pin is symmetrical with respect to rotation and turnable in the insertion channel. The insertion channel always has a shape which is not symmetrical with respect to rotation in order that the screwing-in tool 7 can be inserted in a rotationally fixed manner, but a closure pin with a circular cross-section can still be inserted in a triangular, star-shaped or square insertion channel so that this closure pin rests along a line against the wall of the insertion channel. Rapid turning of the closure pin about its longitudinal axis produces in the region of abutment between insertion channel wall and closure pin as a result of the friction a heating which may lead to melting and welding of the closure pin to the wall material. Such a friction-welding procedure may serve to permanently fix the closure pin in the insertion channel.

In the embodiment illustrated in FIGS. 7 and 8, the bone screw 1 has a continuous insertion channel 5 which terminates in the region of the head 4 of the bone screw 1 in a recess 8 widened in stepped configuration.

The closure pin 8 insertable in this insertion channel 5 has a head-shaped widening 10 which is complementary with the recess 9. The closure pin 8 also carries at the opposite end a longitudinal slot 11 which extends in the axial direction and separates the adjacent wall regions from one another. Outwardly protruding detent noses 12 are held at the end of the closure pin 8. These have slide-on surfaces 13 inclined downwardly in the direction of insertion, while right-angled detent surfaces 14 are arranged on the rear side. When the closure pin 8 is inserted in the insertion channel 5, the detent noses 12 are elastically bent in the direction towards the longitudinal axis of the insertion channel, this elastical bending being made possible by the longitudinal slot 11. Once the closure pin 8 is pushed in completely, the detent noses 12 snap out and rest with their radially protruding detent surfaces 14 against the tip of the bone screw 1 so that the closure pin 8 is held immovably in the axial direction in the bone screw, on the one hand, by these detent noses 12 and, on the other hand, by the widening 10 entering the recess 9.

The embodiment illustrated in FIGS. 9 and 10 differs from that of FIGS. 7 and 8 essentially only in that in this case the closure pin 8 does not carry a longitudinal slot or any outwardly protruding detent noses but instead a detent groove 15 set back with respect to the outside diameter with inclined slide-on surfaces 16 and a radially outwardly protruding detent surface 17. The bone screw, for its part, is provided in the region of its front end with a longitudinal slot 18 and inwardly directed detent projections 19. When the closure pin 8 is fully inserted, these detent projections 19 engage the detent groove 15 and thereby rest against the detent surface 17 in such a way as to prevent the closure pin 8 from moving out of the insertion channel 5. In this case, the longitudinal slot 18 enables an elastic bending-apart of the detent projections 19, i.e., the closure pin 8 forms together with the bone screw 1 an elastic, unreleasable detent connection.

In the embodiment illustrated in FIGS. 11 and 12, detent arms 20 standing vertically upwards with inwardly protruding detent noses 21 at their top end protrude into the recess 9 in the head 4 of the bone screw 1. These detent noses 21 engage behind a radially outwardly protruding detent surface 22 on a thickening 23 of the closure pin 8 and thereby fix the closure pin against being pushed out of the insertion channel. The closure pin 8 is secured against being pushed in too far by a plate-like widening 24 which is supported on the detent arms 20 and thereby closes off the recess 9 (FIG. 12) when the closure pin 8 is inserted.

We claim:

1. A bone screw made of resorbing plastic material, comprising an externally threaded shaft in which a tool insertion channel open at the top, arranged concentrically with said shaft and extending along most of the length of said shaft is located, the cross-section of said insertion channel being non-circular and corresponding to the cross-section of a tool used for screwing-in said screw, characterized by a closure pin made of resorbing material insertable in said insertion channel, thereby filing it out completely, the dimensions of the cross-section of said closure pin being such that it does not expand said screw, whereby the diameter of said screw is at no time enlarged by the insertion of said closure pin.

2. A bone screw as defined in claim 1, characterized in that said insertion channel is closed at the tip of said bone screw.

3. A bone screw as defined in claim 1, characterized in that said insertion channel penetrates said bone screw completely.

4. A bone screw as defined in claim 1, characterized in that the cross-section of said insertion channel is an equilateral triangle.

5. A bone screw as defined in claim 1, characterized in that the cross-section of said insertion channel is a rectangle and preferably a square.

6. A bone screw as defined in claim 1, characterized in that the cross-section of said insertion channel is a regular polygon.

7. A bone screw as defined in claim 1, characterized in that the cross-section of said insertion channel is star-shaped.

8. A bone screw as defined in claim 1, characterized in that said shaft comprises a head-shaped widening at one end and said insertion channel extends through said widening.

9. A bone screw as defined in claim 1, characterized in that said closure pin is fixable with a friction fit in said insertion channel.

10. A bone screw as defined in claim 9, characterized in that said insertion channel or said closure pin taper or widen in cross-section in the direction of insertion.

11. A bone screw as defined in claim 1, characterized in that said closure pin is permanently affixed to said bone screw in said insertion channel.

12. A bone screw made of resorbing plastic material, comprising an externally threaded shaft in which a tool insertion channel open at the top, arranged concentrically with said shaft and extending along most of the length of said shaft is located, the cross-section of said insertion channel being on-circular and corresponding to the cross-section of a tool used for screwing-in said screw, characterized by a closure pin made of resorbing material insertable in said insertion channel, thereby filing it out completely, the dimensions of the cross-section of said closure pin being such that it does not expand said screw, wherein said closure pin is fixable in a positively connected manner in said insertion channel by an elastic detent connection.

13. A bone screw as defined in claim 1, characterized in that said closure pin carries a widening delimiting its screw-in depth.

14. A bone screw as defined in claim 12, characterized in that said closure pin carries a widening delimiting its screw-in depth and said detent connection is arranged in the region of said widening of said closure pin.

15. A bone screw as defined in claim 12, characterized in that said closure pin or said bone screw is slotted in the axial direction in the region of said detent connection.

* * * * *